United States Patent
Olek et al.

(10) Patent No.: US 12,305,237 B2
(45) Date of Patent: May 20, 2025

(54) CXCR3 AS EPIGENETIC MARKER FOR THE IDENTIFICATION OF INFLAMMATORY IMMUNE CELLS, IN PARTICULAR CD8+ MEMORY T CELLS

(71) Applicant: Precision for Medicine GmbH, Berlin (DE)

(72) Inventors: Sven Olek, Berlin (DE); Josephin Held, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 1114 days.

(21) Appl. No.: 17/054,268

(22) PCT Filed: May 10, 2019

(86) PCT No.: PCT/EP2019/061998
§ 371 (c)(1),
(2) Date: Nov. 10, 2020

(87) PCT Pub. No.: WO2019/224014
PCT Pub. Date: Nov. 28, 2019

(65) Prior Publication Data
US 2021/0230698 A1  Jul. 29, 2021

(30) Foreign Application Priority Data
May 25, 2018 (DE) .................. 10 2018 112 644.1

(51) Int. Cl.
C12Q 1/68 (2018.01)
C12Q 1/6883 (2018.01)

(52) U.S. Cl.
CPC ..... *C12Q 1/6883* (2013.01); *C12Q 2600/154* (2013.01); *G01N 2333/7158* (2013.01)

(58) Field of Classification Search
None
See application file for complete search history.

(56) References Cited

FOREIGN PATENT DOCUMENTS

| EP | 3029150 A1 | 6/2016 |
|---|---|---|
| WO | WO 2011/135088 A1 | 11/2011 |
| WO | WO 2012/162660 A2 | 11/2012 |
| WO | 2017050882 A1 | 3/2017 |
| WO | WO 2017/050916 A1 | 3/2017 |
| WO | 2018067869 A1 | 4/2018 |

OTHER PUBLICATIONS

Genbank Accession No. BC034403 (Jul. 2006); NLM, NCBI.*
Jiang et al; Journal of Neuroscience; Jan. 2017, vol. 37, pp. 685-700 (Year: 2017).*
Antequera and Bird, Number of CpG Islands and Genes in Human and Mouse, Proc Natl Acad Sci USA 90: 11995-11999, Dec. 1993.
Booth et al., Quantitative Sequencing of 5-Methylcytosine and t-Hydroxymethylcytosine at Single-Base Resolution Science, May 18, 2012, vol. 336, No. 6083, pp. 934-937.
Esteller, CpG island hypermethylation and tumor Suppressor genes: a booming present, a brighter feature, Oncogene 21:5427-5440, 2002.
Jones and Laird, Cancer Epigenetics Comes of Age, Nature Genetics 21: 163-167, Feb. 1999.
Kristensen and Hansen, PCR-Based Methods for Detecting Single-Locus DNA Methylation Biomarkers in Cancer Diagnostics, Prognostics, and Response to Treatment Clinical Chemistry, 55:8, 1471-1483, 2009.
Kurachi et al., Chemokine Receptor CXCR3 Facilitates CD8)+) T Cell Differentiation Into Short-Lived Effector Cells Leading to Memory Degeneration, Journal of Experimental Medicine Aug. 1, 2011, 208(8): 1605-1620.
Laird, The power and the promise of DNA methylation markers, Nature Reviews/Cancer 3:253-266, Apr. 1, 2003.
Lleo et al., DNA methylation profiling of the X chromosome reveals an aberrant demethylation on CXCR3 promoter in primary biliary cirrhosis, Clinical Epigenetics, vol. 7, No. 1, Jul. 7, 2015.
Samji T. et al., Understanding memory CD8+ T cells, Immunol Letter May 2017, 185: 32-39.
Queiros et al: Decoding the DNA Methylome of Mantle Cell Lymphoma in the Light of the Entire B Cell Lineage, Cancer Cell (2016) 30 (5) 806-821.

* cited by examiner

*Primary Examiner* — Jehanne S Sitton
(74) *Attorney, Agent, or Firm* — BakerHostetler

(57) ABSTRACT

The present invention relates to a method, in particular an in vitro method, for specifically identifying the C-X-C motif chemokine receptor 3 (CXCR3) subpopulation of immune cells in a sample from a mammal comprising immune cells, in particular at least one of CD8+ effector and memory T cells, T helper (Th)1 cells and natural killer T (NKT) cells, comprising analyzing epigenetic modifications/properties of (including the methylation status) of at least one CpG position in the mammalian gene region for CXCR3 according to SEQ ID No. 1, wherein a demethylation or lack of methylation of said of at least one CpG position in said gene region is indicative for said CXCR3 specific subpopulation of immune cells in said sample, when compared to other immune cells, in particular for at least one of CD8+ effector and memory T cells, T helper (Th)1 cells and natural killer T (NKT) cells. The analyses according to the invention can identify the above cells on an epigenetic level and distinguish them from all other cells in complex samples, such as, for example, other blood or immune cells. The present invention furthermore provides an improved method for quantifying the above cells, in particular in complex samples. The method can be performed without a step of purifying and/or enriching cells, preferably in whole blood and/or non-trypsinized tissue.

11 Claims, 3 Drawing Sheets
Specification includes a Sequence Listing.

Figure 2

Sequences of Amplicon:

Genomic (SEQ ID NO: 1):
GGTGCAGTCCTCAGAGCTGGGAGGTGCTTCCCGGAGAGACCTGGTGCTGCTGGGCTGCCAGTGAGTCCCGGAGCGAGGATATT
GGGAGAGCCAGAGCCGGCAGAGGAGGAGCCTGGAATGCGGGAAGTCAGACTGTGGGCGAAAGGGAGCCCGGATTCC
GGCCTCACAAGCCCGAGTAGGAGGCCTCTGAGGTCTCAGACCAGGATGAATCCCGGCGGGAAGACGATGCTGCCTCTGAGCCCT
CTCTGGTTGGGGCAGCCCAGGCGCAAGAGCAGCATCCACATCCGCTCCCGAACTTGACCCCTACAAAGGCATAGAGCAGCGGGTT
GAGGCAGCAGTGCATGTAGCCCAGGCCTGAGGTGACCGACTTGGCCACGTCTACCCTGCTTTCTCGGCCACAGTTGCGGGCCAAAGC
GCCCAGGTCCATGAGGATGTCCACCAGCACCACCAGGTGATAGGGGTCCAG CpG Template Variant (methylated, i.e. non-converted CGs) (SEQ ID NO: 2):
GGTGTAGTTTTTAGAGTTGGGAGGTGTTTTCGGGAGAGTTGGTGTTGTTGGGTTGTTAGTGAGTTTCGGGAGCGAGGATATTGG
GGAGAGTTAGAGTCGGTAGAGGAGGAGTTTGGAATGCGGGAAGTTAGATTGTGGGCGAAAGGGAGTTCGGATTTCGGT
TTTATAAGTTCGAGTAGGAGGTTTTTGAGGTTTTAGATTAGGATGAATTCGGCGGGAAGACGATGTTGTTTTTGGAGTTTTTTGG
TTGGGTAGTTTAGGCGTAAGAGTAGTATTTATAAAGGTATAGAGTAGCGGGTTGAGGTAGTAG
TGTATGTAGTTAGTTTGAGGTTTGAGGTGATCGATTGGTTACGTTTATTTGTTTTTCGGTTATAGTTGCGGGTTAAAGCGTTTAGGTTTATGA
GGATGTTTATTAGTATTATTAGGTGATAGGGGTTTAG TpG Template Variant (un-methylated, i.e. converted CGs) (SEQ ID NO: 3):
GGTGTAGTTTTTAGAGTTGGGAGGTGTTTTTGGGAGAGTTGGTGTTGTTGGGTTGTTAGTGAGTTTTGGGAGTGAGGATATTGG
GGAGAGTTAGAGTTGGTAGAGGAGGAGTTTGGAATGTGGGAAGTTAGATTGTGGGTGAAAGGGAGTTTGGATTTTGGTT
TTATAAGTTTGAGTAGGAGGTTTTTGAGGTTTTAGATTAGGATGAATTTGGTGGGAAGATGATGTTGTTTTTGGAGTTTTTTGGT
TGGGTAGTTTAGGTGTAAGAGTAGTATTTATAAAGGTATAGAGTGGGTTGAGGTAGTAGT
GTATGTAGTTAGTTTGAGGTTTGAGGTGATTGATTGGTTATGTTTATTTGTTTTTTGGTTATAGTTGTGGGTTAAAGTGTTTAGGTTTATGAG
GATGTTTATTAGTATTATTAGGTGATAGGGGTTTAG

SEQUENCE LISTING

<160> NUMBER OF SEQ ID NOS: 9

<210> SEQ ID NO 1
<211> LENGTH: 481
<212> TYPE: DNA
<213> ORGANISM: Homo sapiens

<400> SEQUENCE: 1

```
ggtgcagtcc tcagagctgg gagggtggct tcccgggaga cctggtggtg ctggggctgc      60
cagtgagtcc cgggagcgag gatattgggg agagccagag ccgcagagg gagggaggag     120 cctggaatgc ggggaagtca gactgtgggc gaaaggggag cccggattcc ggcctcacaa     180
gcccgagtag gaggcctctg aggtctcaga ccaggatgaa tccggcggg aagacgatgg     240 ctgcctctgg agccctctct ggttgggca gcccaggcgc aagagcagca tccacatccg     300
ctcccggaac ttgacccta caaaggcata gagcagcggg ttgaggcagc agtgcatgta     360
gcccaggcct gaggtgaccg acttggccac gtctaccctg ctttctcggc cacagttgcg     420
ggccaaagcg cccaggtcca tgaggatgtc caccagcacc accaggtgat agggggtcca     480
g                                                                     481
```

<210> SEQ ID NO 2
<211> LENGTH: 481
<212> TYPE: DNA
<213> ORGANISM: Homo sapiens

<400> SEQUENCE: 2

```
ggtgtagttt ttagagttgg gagggtggtt tttcgggaga tttggtggtg ttggggttgt      60
tagtgagttt cgggagcgag atattgggg agagttagag tcggtagagg gagggaggag     120 tttgaatgc ggggaagtta gattgtgggc gaaaggggag ttcggatttc ggttttataa     180
gttcgagtag gaggttttg aggttttaga ttaggatgaa tttcggcggg aagacgatgg     240 ttgttttgg agttttttt ggttgggta gtttaggcgt aagagtagta tttatattcg      300
ttttcggaat ttgatttta taaaggtata gagtagcggg ttgaggtagt agtgtatgta     360
gtttaggttt gaggtgatcg atttggttac gtttattttg ttttttcggt tatagttgcg     420
ggttaaagcg tttaggttta tgaggatgtt tattagtatt attaggtgat aggggttta      480 g                                                                    481
```

<210> SEQ ID NO 3
<211> LENGTH: 481
<212> TYPE: DNA
<213> ORGANISM: Homo sapiens

<400> SEQUENCE: 3

```
ggtgtagttt ttagagttgg gagggtggtt ttttgggaga tttggtggtg ttggggttgt     60
tagtgagttt tgggagtgag atattgggg agagttagag ttggtagagg gagggaggag    120 tttgaatgt ggggaagtta gattgtgggt gaaagggag tttggatttt ggttttataa     180
gtttgagtag gaggttttg aggttttaga ttaggatgaa ttttgtggg aagatgatgg     240 ttgttttgg agttttttt ggttgggta gtttaggtgt aagagtagta tttatatttg      300
tttttggaat ttgatttta taaaggtata gagtagtggg ttgaggtagt agtgtatgta     360
gtttaggttt gaggtgattg atttggttat gtttattttg ttttttggt tatagttgtg     420 ggttaaagtg tttaggttta tgaggatgtt tattagtatt attaggtgat aggggttta     480 g                                                                    481
```

<210> SEQ ID NO 4
<211> LENGTH: 18
<212> TYPE: DNA
<213> ORGANISM: Homo sapiens

<400> SEQUENCE: 4

```
gggtgaaagg ggagtttg                                                   18
```

<210> SEQ ID NO 5
<211> LENGTH: 30
<212> TYPE: DNA
<213> ORGANISM: Homo sapiens

<400> SEQUENCE: 5

```
caaaaacaaa tataaatact actcttacac                                      30
```

<210> SEQ ID NO 6
<211> LENGTH: 27
<212> TYPE: DNA
<213> ORGANISM: Homo sapiens

<400> SEQUENCE: 6

```
tgaattttgg tgggaagatg atggttg                                    27

<210> SEQ ID NO 7
<211> LENGTH: 16
<212> TYPE: DNA
<213> ORGANISM: Homo sapiens

<400> SEQUENCE: 7
gcgaaagggg agttcg                                                16

<210> SEQ ID NO 8
<211> LENGTH: 30
<212> TYPE: DNA
<213> ORGANISM: Homo sapiens

<400> SEQUENCE: 8
cgaaaacgaa tataaatact actcttacgc                                 30

<210> SEQ ID NO 9
<211> LENGTH: 24
<212> TYPE: DNA
<213> ORGANISM: Homo sapiens

<400> SEQUENCE: 9
atttcggcgg gaagacgatg gttg                                       24
```

CXCR3 AS EPIGENETIC MARKER FOR THE IDENTIFICATION OF INFLAMMATORY IMMUNE CELLS, IN PARTICULAR CD8+ MEMORY T CELLS

CROSS-REFERENCE TO RELATED APPLICATIONS

This application is a 35 U.S.C. § 371 national phase application of International Patent Application No. PCT/EP2019/061998, filed May 10, 2019, which claims priority to German Patent Application No. 10 2018 112 644.1, filed May 25, 2018, the entire disclosures of each of which are incorporated herein by reference in their entirety.

The Sequence Listing for this application is labeled "113828.000025 Sequence Listing.txt", which was created on Oct. 30, 2020 and is 4 Kilobytes. The entire content is incorporated herein by reference in its entirety.

The present invention relates to a method, in particular an in vitro method, for specifically identifying the C-X-C motif chemokine receptor 3 (CXCR3) subpopulation of immune cells in a sample from a mammal comprising immune cells, in particular at least one of CD8+ effector and memory T cells, T helper (Th)1 cells and natural killer T (NKT) cells, comprising analyzing epigenetic modifications/properties of (including the methylation status) of at least one CpG position in the mammalian gene region for CXCR3 according to SEQ ID No. 1, wherein a demethylation or lack of methylation of said of at least one CpG position in said gene region is indicative for said CXCR3 specific subpopulation of immune cells in said sample, when compared to other immune cells, in particular for at least one of CD8+ effector and memory T cells, T helper (Th)1 cells and natural killer T (NKT) cells. The analyses according to the invention can identify the above cells on an epigenetic level and distinguish them from all other cells in complex samples, such as, for example, other blood or immune cells. The present invention furthermore provides an improved method for quantifying the above cells, in particular in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure the CXCR3 specific subpopulation of immune cells, such as CD8+ effector and memory T cells, T helper (Th)1 cells and natural killer T (NKT) cells of the blood within any solid organs, tissue or body fluid of a mammal.

BACKGROUND OF THE INVENTION

CD8+ memory T cells, T helper (Th)1 cells and natural killer T cells (NKT) are important subsets of infection- and cancer-fighting T cells (see, for example, Samji T and Khanna K M. Understanding memory CD8+ T cells. Immunol Lett. 2017 May; 185:32-39). CD8+ memory T cells can be subdivided into effector (CD3+, CD8+, CD45RA+, CCR7−; CD40L−), effector memory (CD3+, CD8+, CD45RA−, CCR7−; CD40L−), and central memory (CD3+, CD8+, CD45RA+, CCR7+; CD40L−) CD8+ T cells. T helper (Th)1 cells are CD3+, CD4+, CD45RA−, CCR6− and CXCR3+, and natural killer T cells (NKT) are CD3+, CD8+, CD56+.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics-heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90:11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

Kurachi et al. (in: Kurachi et al. Chemokine receptor CXCR3 facilitates CD8(+) T cell differentiation into short-lived effector cells leading to memory degeneration. J Exp Med. 2011 Aug. 1; 208 (8): 1605-20. doi: 10.1084/jem.20102101. Epub 2011 Jul. 25) disclose that the strength of inflammatory stimuli during the early expansion phase plays a crucial role in the effector versus memory cell fate decision of CD8(+) T cells. They demonstrate that the chemokine receptor CXCR3 is involved in promoting CD8 (+) T cell commitment to an effector fate rather than a memory fate by regulating T cell recruitment to an antigen/inflammation site. After systemic viral or bacterial infection, the contraction of CXCR3 (−/−) antigen-specific CD8(+) T cells is significantly attenuated, resulting in massive accumulation of fully functional memory CD8(+) T cells. Early after infection, CXCR3 (−/−) antigen-specific CD8(+) T cells fail to cluster at the marginal zone in the spleen where inflammatory cytokines such as IL-12 and IFN-α are abundant, thus receiving relatively weak inflammatory stimuli. Consequently, CXCR3 (−/−) CD8(+) T cells exhibit transient expression of CD25 and preferentially differentiate into memory precursor effector cells as compared with wild-type CD8(+) T cells. This series of events has important implications for development of vaccination strategies to generate increased numbers of antigen-specific memory CD8(+) T cells via inhibition of CXCR3-mediated T cell migration to inflamed microenvironments.

Lleo et al. (in: Lleo et al. DNA methylation profiling of the X chromosome reveals an aberrant demethylation on CXCR3 promoter in primary biliary cirrhosis) describe that primary biliary cirrhosis (PBC) is rigorously defined by the X chromosome methylation profile of CD4+, CD8+, and CD14+ cells as studies in 30 PBC patients and 30 controls. Genomic DNA from sorted CD4+, CD8+, and CD14+ subpopulations was isolated, sonicated, and immunoprecipitated for analysis of methylation. All products were hybridized to a custom-tiled four-plex array containing 27,728 CpG islands annotated by UCSC and 22,532 well-characterized RefSeq promoter regions. Furthermore, bisulfite sequencing was then used for validation on a subsequent group of independent samples from PBC patients and controls. Thence, expression levels of selected X-linked genes were evaluated by quantitative real-time PCR with cDNA samples from all subjects. A total of 20, 15, and 19 distinct gene promoters reflected a significant difference in DNA methylation in CD4+T, CD8+T, and CD14+ cells in patients with PBC. Interestingly, there was hypermethylation of FUNDC2 in CD8+ T cells and a striking demethylation of CXCR3 in CD4+ T cells, which inversely correlated with CXCR3 expression levels in CD4+ T cells from early-stage PBC patients. The data provides a set of genes with epigenetic alteration likely to be indicators of autoimmunity and emphasizes the role of CXCR3 in the natural history of PBC.

In view of the above, it is an object of the present invention to provide an improved and in particular robust method based on DNA-methylation analysis as a superior tool in order to more conveniently and reliably detect, identify, discriminate, and quantify the CXCR3+ specific subpopulation of immune cells, such as CD8+ memory T cells, T helper (Th)1 cells and natural killer T cells (NKT).

The present invention solves the above object by providing a method for specifically identifying the C-X-C motif chemokine receptor 3 (CXCR3) subpopulation of immune cells in a sample from a mammal comprising immune cells, comprising analyzing the methylation status of at least one CpG position in the mammalian gene region for CXCR3 according to SEQ ID No. 1, wherein a demethylation or lack of methylation of said of at least one CpG position in said gene region is indicative for said CXCR3 specific subpopulation of immune cells in said sample, when compared to other immune cells.

Preferred is a method, wherein said subpopulation of CXCR3 specific immune cells comprises at least one of CD8+ effector and memory T cells, T helper (Th)1 cells and natural killer T (NKT) cells, and is compared to an immune cell other than a CD8+ memory or effector T cell, T helper (Th)1 cell and/or natural killer T (NKT) cell. All the cells as identified belong to the CXCR3+ specific subpopulation of immune cells.

CXCR3 is able to regulate leukocyte trafficking. Binding of chemokines to CXCR3 induces various cellular responses, most notably integrin activation, cytoskeletal changes and chemotactic migration. CXCR3-ligand interaction attracts Th1 cells and promotes Th1 cell maturation. As a consequence of chemokine-induced cellular desensitization (phosphorylation-dependent receptor internalization), cellular responses are typically rapid and short in duration. Cellular responsiveness is restored after dephosphorylation of intracellular receptors and subsequent recycling to the cell surface. A hallmark of CXCR3 is its prominent expression in in vitro cultured effector/memory T cells, and in T cells present in many types of inflamed tissues; CXCR3 is rapidly induced on naïve cells following activation and preferentially remains highly expressed on Th1-type CD4+ T cells and effector CD8+ T cells. In addition, CXCL9, CXCL10 and CXCL11 are commonly produced by local cells in inflammatory lesion, suggesting that CXCR3 and its chemokines participate in the recruitment of inflammatory cells. The gene for human CXCR3 is found on chromosome X; Ensembl-ID: ENSG00000186810.

The present invention is further based on the surprising identification of a region of the CXCR3 gene by the inventors, as specific epigenetic marker, allowing the thus also specific identification of the CXCR3 specific subpopulation of immune cells, such as CD8+ memory or effector T cells, T helper (Th)1 cells and/or natural killer T (NKT) cells as well as the clinical routine application of said analysis.

Surprisingly, the discriminatory pattern of bisulfite convertible and non-convertible cytosine is particularly and even exclusively limited to the genomic region according to SEQ ID No. 1 for the CXCR3 specific subpopulation of immune cells, in particular CD8+ memory or effector T cells, T helper (Th)1 cells and/or natural killer T (NKT) cells as shown using the amplicon according to SEQ ID No. 1, and in particular in the bisulfite converted sequences according to SEQ ID No. 2 and/or 3 (CpG converted and TpG converted sequences for AMP 3188).

The inventors could specifically demonstrate that in the CD8+ memory or effector T cells, T helper (Th)1 cells and/or natural killer T (NKT) cells the CpG motifs as disclosed are almost completely demethylated (i.e. to more than 70%, preferably 80%, preferably, more than 90% and most preferred more than 95%), whereas the same motifs are completely methylated in non-CD8+ memory or effector T cells, non-T helper (Th)1 cells and/or non-natural killer T (NKT) cells. As a preferred embodiment, the method provides an identification of CD8+ effector and memory T cells, wherein the CpG motifs as disclosed are completely demethylated, i.e. to more than 95%). This allows for a distinction and identification of said CD8+ effector and memory T cells from all other cells in said sample. As a preferred embodiment, the method further comprises the steps of pre-sorting said sample based on the immune cell marker CD4, and a subsequent step of specifically identifying T helper (Th)1 cells, based on said analyzing of the methylation status.

The differential methylation of the CpG motifs within the aforementioned regions is a valuable tool to identify the subpopulation of CXCR3 specific immune cells, such as CD8+ memory or effector T cells, T helper (Th)1 cells and/or natural killer T (NKT) cells, such as will be required/ or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of the subpopulation of CXCR3 specific immune cells, e.g. CD8+ memory or effector T cells, T helper (Th)1 cells and/or natural killer T (NKT) cells without purification or any staining procedures.

Another preferred aspect of the method according to the present invention then further comprises a quantification of the relative amount of the cells of the subpopulation of CXCR3 specific immune cells, preferably CD8+ memory or effector T cells, T helper (Th)1 cells and/or natural killer T (NKT) cells based on comparing relative amounts of said methylation frequency in the region as analyzed with relative amounts of the methylation frequency in a, preferably fully demethylated, control gene, such as, for example, GAPDH. Said quantification is thus achieved based on the ratio of the bisulfite convertible DNA to non-convertible DNA in the genetic region of CXCR3 (e.g. of SEQ ID No. 1) as described and analyzed herein. Most preferred is a quantification of the relative amount of the subpopulation of CXCR3 specific immune cells, in particular CD8+ memory or effector T cells, T helper (Th)1 cells and/or natural killer T (NKT) cells is based on an (preferably parallel or simultaneous) analysis of the relative amount of bisulfite convertible DNA of CXCR3, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID No. 1, preferably oligomers according to any of SEQ ID No. 4 to 9.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, pyrosequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the CXCR3 gene region is produced that is a particularly preferred "tool" for performing the method(s) according to the present invention. Consequently, oligomers according to any of SEQ ID No. 4 to 9 or an amplicon as amplified by a primer pair based on SEQ ID No. 4 and 6 or 7 and 9 as mentioned herein constitute preferred embodiments of the present invention. Thus, the sequence of SEQ ID No. 1 (and, if needed, the complementary sequences thereto) can be used to design primers for amplifications, i.e. serve as "beacons" in the sequence as relevant. Similarly, additional primers and probes can be designed based on the amplicon according to SEQ ID No. 1. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID No. 1, and is preferably selected from the CpG positions 34, 71, 77, 102, 130, 150, 163, 170, 184, 224, 227, 235, 278, 299, 305, 337, 379, 390, 407, 419, and 429 in the amplicon 3188 according to SEQ ID No. 1. Preferred are combinations of 3, 4, 5, 6, 7, 8, 9, or 10 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position 71, 77, 102, 130, 150, 163, 170, and 184 for all the three cell types as to be identified, or at least one of 224, 227, 235, 278, 299, 305, and 337 for CD8+ T cells in the amplicon No. 3188 of the specific bisulfite convertible region (SEQ ID No. 1), or all sites as present on the bisulfite convertible region according to SEQ ID No 1. One or more of positions 102, and/or 184 in AMP 3188 may be excluded.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, pyrosequencing, an analysis selected from promoter methylation, CpG island methylation, MSP, HeavyMethyl, MethylLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said subpopulation of CXCR3 specific immune cells, in particular CD8+ memory and effector T cells, T helper (Th)1 cells and natural killer T cells (NKT), and preferably of Th1 cells, CD8+ memory and effector T cells from all major peripheral blood cell types and/or non-blood cells, preferably, but not limited to, cytotoxic T-cells, granulocytes, monocytes, B-cells, CD56++ NK cells, and other T-helper cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, goat, dog, pig, cat, cow rat, monkey or human. The samples can be suitably pooled, if required.

Another preferred aspect of the method according to the present invention then further comprises the step of concluding on the immune status of said mammal based on said subpopulation of CXCR3 specific immune cells as identified, such as CD8+ memory and effector T cells, T helper (Th)1 cells and natural killer T cells (NKT), and preferably said CD8+ memory and effector T cells. These cells can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to *Trypanosoma cruzi*-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of the subpopulation of CXCR3 specific immune cells, in particular of at least one of CD8+ effector and memory T cells, T helper (Th)1 cells and natural killer T (NKT) cells in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said subpopulation of CXCR3 specific immune cells, e.g. at least one of CD8+ effector and memory T cells, T helper (Th)1 cells and natural killer T (NKT) cells as e.g. a sample for cell transfer into a patient.

Another preferred aspect of the method according to the present invention then relates to a method as above, further comprising formulating said subpopulation of CXCR3 specific immune cells, in particular at least one of CD8+ effector and memory T cells, T helper (Th)1 cells and natural killer T (NKT) cells as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID No. 4 to 9, or an amplicon according to SEQ ID No. 1 to 3.

Yet another preferred aspect of the present invention then relates to a kit for identifying, quantifying, and/or monitoring the C-X-C motif chemokine receptor 3 (CXCR3) subpopulation of immune cells, preferably CD8+ effector and memory T cells, T helper (Th)1 cells and natural killer T (NKT) cells, and more preferably CD4+Th1 cells, or CD8+ effector and memory T cells, in a mammal based on the analysis of the bisulfite accessibility of CpG positions in the gene region of CXCR3, comprising components for performing a method according to invention as described herein, in particular a kit comprising a) a bisulfite reagent, and b) materials for the analysis of the methylation status of CpG positions selected from the CpG positions in the region according to SEQ ID NO: 1, such as an oligomer selected from the sequences according to SEQ ID No. 4 to 9.

The present invention also encompasses the use of oligomers or amplicon or a kit according to the present invention for identifying, quantifying, and/or monitoring the C-X-C motif chemokine receptor 3 (CXCR3) subpopulation of immune cells, preferably CD8+ effector and memory T cells, T helper (Th)1 cells and natural killer T (NKT) cells, and more preferably CD4+Th1 cells, or CD8+ effector and memory T cells, in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=a/b
a=Σ (C and/or mC and/or hmC and/or fC and/or cC)
b=Σ (C and/or mC and/or hmC and/or fC and/or cC),
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the CXCR3 genetic region and in particular the amplicon as described herein as a marker, the inventors very specifically identified, quantified and particularly differentiated the C-X-C motif chemokine receptor 3 (CXCR3) subpopulation of immune cells, preferably of at least one of CD8+ effector and memory T cells, T helper (Th)1 cells and natural killer T (NKT) cells, and in their relation to other cell types in a sample, for example to other blood and/or immune cells.

The invention will now be further described in the following examples and with reference to the accompanying figures and the sequence listing, without being limited thereto. For the purposes of the present invention, all references as cited herein are incorporated by reference in their entireties.

FIG. 1 shows the analysis of CpG sites on amplicon No. 3188 (SEQ ID No. 2) according to the invention. The horizontal boxes in the table correspond to the CpG positions in the amplicon as analyzed (e.g. CpG 1, 2, etc.) with the positions indicated (AMP3188: 34 corresponding to CpG 1 of Amplicon 3188 . . . , etc.), and the columns correspond to the cell types as analyzed. BLC—B cells; CTL—cytotoxic T cells; GRC—granulocytes; MOC—monocytes; NKC—natural killer cells; T4m—CD4+ central memory cells; T4n—CD4+ naïve T cells; T8m—CD8+ central memory T cells; T8n—CD8+ naïve T cells; THC-T helper cells; THE-T helper cells type 1; and THZ-T helper cells type 2.

FIG. 2 shows the sequences of the amplicon 3188 of the invention. Primer and probe sequences are indicated (underlined, double underlined, respectively), CpG positions are bold.

Figure 3:
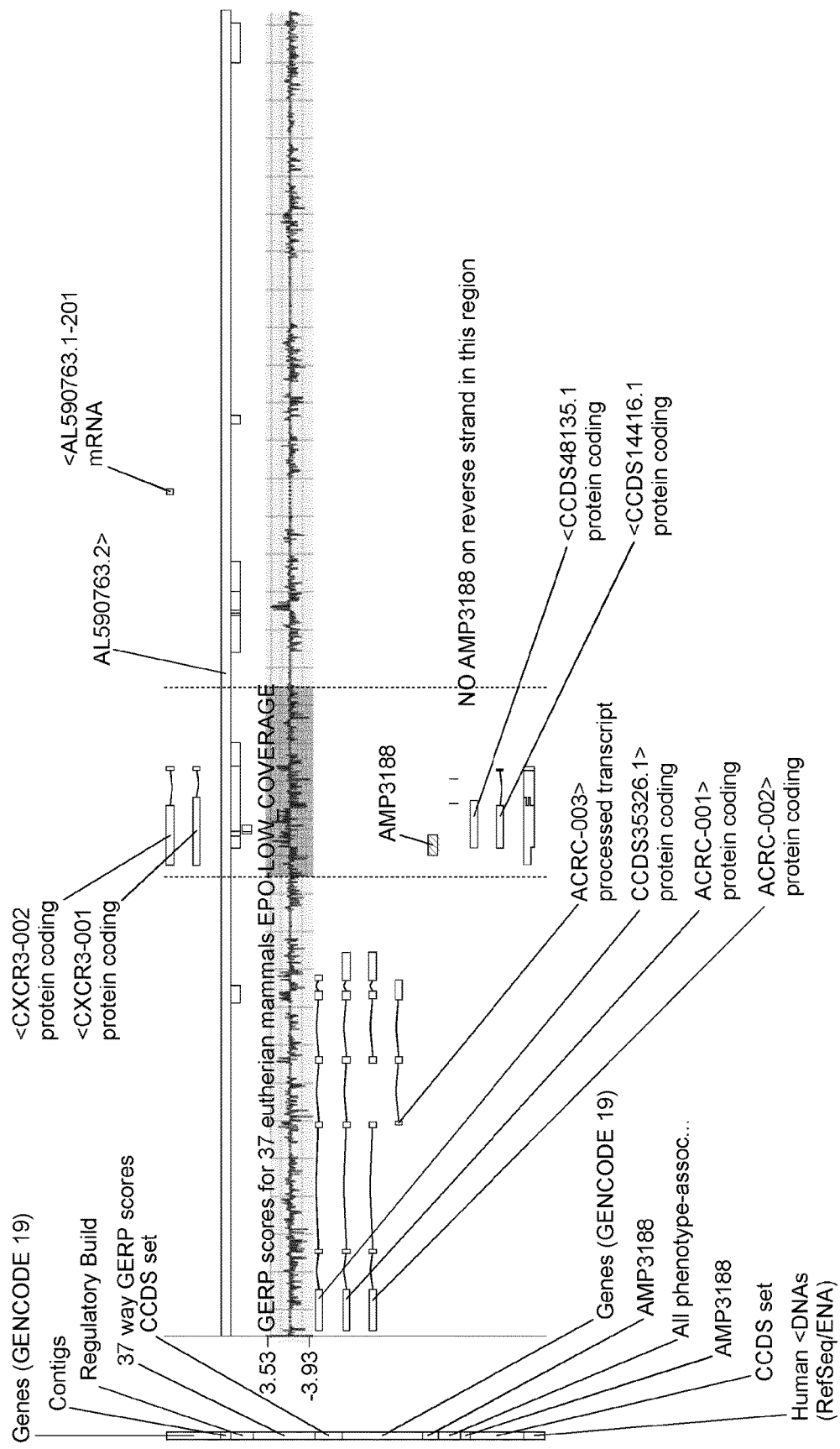
FIG. 3 shows the genomic region of the amplicon according to the present invention, the amplicon 3188 position is shown as a box.

SEQ ID No. 1 shows the sequence of the amplicon No. 3188 according to the present invention (see FIG. 3).

SEQ ID Nos. 2 and 3 show the sequences of the CpG converted and TpG converted sequences of amplicon 3188, respectively.

SEQ ID Nos. 4 to 9 show the sequences of specific oligomers (primers and probes) according to the present invention.

EXAMPLES

Example 1

Figure 1:
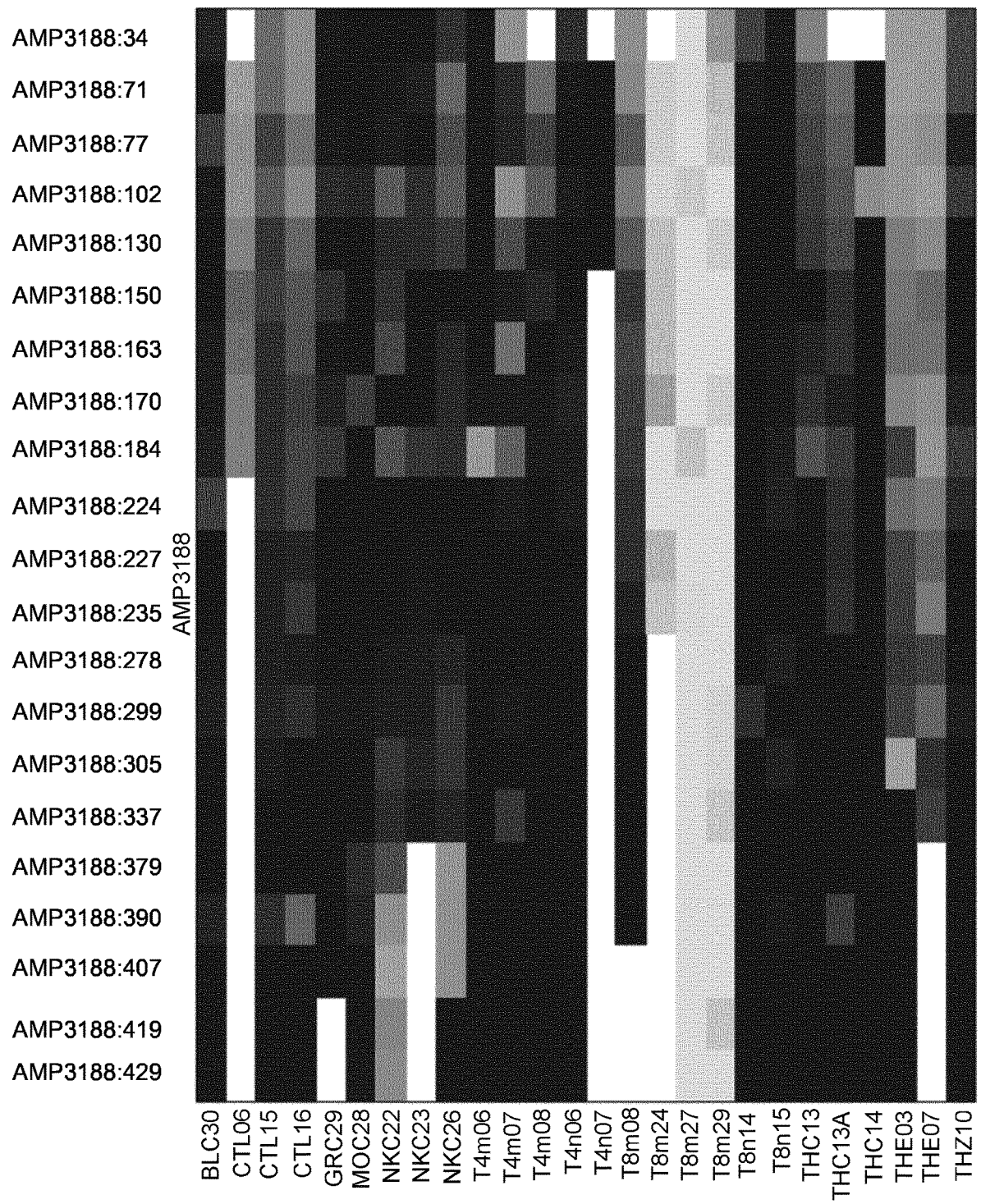

In order to identify CD8+ memory and effector T cells, T helper (Th)1 cells and natural killer T cells (NKT), qPCR was performed on bisulphite converted samples stemming from the human genomic region according to the sequence SEQ ID No. 1, in particular the region of AMP 3188. For the actual epigenetic profiling of the amplicon region in blood cell subtypes, the immune cell populations as analyzed were as shown in FIG. 1.

The bisulfite-converted target-regions of preferred qPCR-assay-system as developed were (see also FIG. 2):

```
CpG Template Variant (methylated, i.e. non-
converted CGs) (SEQ ID NO: 2):
GGTGTAGTTTTTAGAGTTGGGAGGGTGGTTTTTCGGGAGATTTGGTGGT

GTTGGGGTTGTTAGTGAGTTTCGGGAGCGAGGATATTGGGGAGAGTTAG

AGTCGGTAGAGGGAGGGAGGAGTTTGGAATGCGGGGAAGTTAGATTGTG

GGCGAAAGGGGAGTTCGGATTTCGGTTTTATAAGTTCGAGTAGGAGGTT

TTTGAGGTTTTAGATTAGGATGAATTTCGGCGGGAAGACGATGGTTGTT

TTTGGAGTTTTTTTTGGTTGGGGTAGTTTAGGCGTAAGAGTAGTATTTA

TATTCGTTTTCGGAATTTGATTTTTATAAAGGTATAGAGTAGCGGGTTG

AGGTAGTAGTGTATGTAGTTTAGGTTTGAGGTGATCGATTTGGTTACGT

TTATTTTGTTTTTCGGTTATAGTTGCGGGTTAAAGCGTTTAGGTTTAT

GAGGATGTTTATTAGTATTATTAGGTGATAGGGGGTTTAG

TpG Template Variant (un-methylated, i.e.
converted CGs) (SEQ ID NO: 3):
GGTGTAGTTTTTAGAGTTGGGAGGGTGGTTTTTGGGAGATTTGGTGGT

GTTGGGGTTGTTAGTGAGTTTTGGGAGTGAGGATATTGGGGAGAGTTAG

AGTTGGTAGAGGGAGGGAGGAGTTTGGAATGTGGGGAAGTTAGATTGTG

GGTGAAAGGGGAGTTTGGATTTTGGTTTTATAAGTTTGAGTAGGAGGTT

TTTGAGGTTTTAGATTAGGATGAATTTTGGTGGGAAGATGATGGTTGTT

TTTGGAGTTTTTTTTGGTTGGGGTAGTTTAGGTGTAAGAGTAGTATTTA

TATTTGTTTTTGGAATTTGATTTTTATAAAGGTATAGAGTAGTGGGTTG

AGGTAGTAGTGTATGTAGTTTAGGTTTGAGGTGATTGATTTGGTTATGT

TTATTTTGTTTTTTGGTTATAGTTGTGGGTTAAAGTGTTTAGGTTTAT

GAGGATGTTTATTAGTATTATTAGGTGATAGGGGGTTTAG
```

Preferred assay conditions were as follows:

TpG system:

| | |
|---|---|
| Primer: | 1.5 µM final Concentration |
| Probe: | 0.125 µM final Concentration |

-continued

| | |
|---|---|
| Working Solution Probe (20x): | 2.5 μM |
| Working Solution Primer Mix (20x): | 30 μM |
| Working Solution λ-DNA (10x): | 50 ng/μl |
| Additive (e.g. Mg$^{2+}$): | -μM Final Concentration |
| Roche Master-Mix: | 1x |
| Reaction Volume: | 10 μl |
| Thermo Profile: | |
| Pre-Incubation: | 95° C. for 35 min. |
| Annealing/Elongation: | 61° C. for 15 sec. |
| Denaturation: | 95° C. for 1 min. |
| No of Cycles: | 50 |
| CpG System: | |
| Primer: | 1.5 μM Final Concentration |
| Probe: | 0.125 μM Final Concentration |
| Working Solution Probe (20x): | 2.5 μM |
| Working Solution Primer Mix (20x): | 30 μM |
| Working Solution λ-DNA (10x): | 50 μg/ul |
| Additive (e.g. Mg$^{2+}$): | -μM Final Concentration |
| Roche Master-Mix: | 1x |
| Reaction Volume: | 10 μl |
| Thermo Profile: | |
| Pre-Incubation: | 95° C. for 35 min. |
| Annealing/Elongation: | 61° C. for 15 sec. |
| Denaturation: | 95° C. for 1 min. |
| No of Cycles: | 50 |

The preferred primer and probe sequences were:

| TpG-System | Sequence 5' → 3' + optional modifications |
|---|---|
| Primer_FW | GGGTGAAAGGGGAGTTTG (SEQ ID NO: 4) |
| Primer_Rv | CAAAACAAATATAAATACTACTCTTACAC (SEQ ID NO: 5) |
| Probe | FAM -TGAATTTTGGTGGGAAGATGATGGTTG - BHQ1 (SEQ ID NO: 6) |

| CpG-System | Sequence 5' → 3' + optional modifications |
|---|---|
| Primer_FW | GCGAAAGGGGAGTTCG (SEQ ID NO: 7) |
| Primer_Rv | CGAAAACGAATATAAATACTACTCTTACGC (SEQ ID NO: 8) |
| Probe | FAM - ATTTCGGCGGGAAGACGATGGTTG - BHQ1 (SEQ ID NO: 9) |

FAM—fluorescein

BHQ1—non-fluorescent Black Hole Quencher®-1 (Sigma Aldrich)

Results:

Following the successful application of the assay as above, the following demethylation levels were found in amplicon 3188 for the cell types of interest:

| | % demethylation CXCR3 (amplicon 3188) |
|---|---|
| Total CD8+ T cells | 43.2 |
| Naive CD8+ T cells | 2.4 |
| Effector CD8+ T cells | 100.7 |
| Effector memory CD8+ T cells | 110.5 |
| Central memory CD8+ T cells | 91.2 |
| Total CD4+ T cells | 23.8 |
| Naive CD4+ T cells | 0.9 |
| Effector CD4+ T cells (TH1) | 79.9 |
| Effector CD4+ T cells (TH2) | 7.2 |
| Memory CD4+ T cells | 29.7 |
| NK Cells | 1.5 |
| NKT cells | 82.1 |
| Granulocytes | 1.5 |
| Monocytes | 0.2 |
| B-cells | 1.7 |
| p-dendritic cells | 3.6 |
| m-dendritic cells | 4.4 |

The invention claimed is:

1. A method for producing an amplicon from a gene region of the human C-X-C motif chemokine receptor 3 (CXCR3) gene, the method comprising:
   a) bisulfite treating isolated genomic DNA comprising SEQ ID NO: 1 to generate bisulfite treated DNA, wherein the isolated genomic DNA is from a human cell sample comprising CD8+ memory T cells,
   b) producing the amplicon by amplifying from a region of the bisulfite treated DNA comprising SEQ ID NO: 1 prior to bisulfite treatment, and
   c) detecting, in the amplicon, TpG at at least one of CpG positions 150, 163, 170, and 184 relative to SEQ ID NO: 1 prior to bisulfite treatment.

2. The method according to claim 1, further comprising detecting, in the amplicon, TpG at at least one of CpG positions 34, 71, 77, 102, 130, 224, 227, 235, 278, 299, 305, 337, 379, 390, 407, 419, and 429 relative to SEQ ID NO: 1 prior to bisulfite treatment.

3. The method according to claim 1, wherein the TpG is detected by a method selected from a methylation specific enzymatic digest, bisulfite sequencing, promoter methylation analysis, CpG island methylation analysis, MSP, HeavyMethyl, MethyLight, Ms-SNuPE, and other methods relying on a detection of amplified DNA.

4. The method according to claim 1, wherein said human cell sample is selected from a body fluid, a blood sample, a tissue, an organ, a cell type blood sample, or a sample of blood lymphocytes.

5. The method according to claim 1, wherein the method is performed without a step of purifying and/or enriching the human cell sample.

6. The method according to claim 1, wherein said human cell sample is from a human who suffers from or is likely to suffer from autoimmune diseases, transplant rejections, infectious diseases, cancer, and/or allergy.

7. The method according to claim 1, wherein the method is performed using a kit comprising a) a bisulfite reagent, and b) materials for producing the amplicon.

8. The method of claim 1, wherein the amplifying is performed with an oligomer according to any of SEQ ID NOs: 4 to 9.

9. The method according to claim 7, wherein the materials comprise an oligomer comprising the sequence selected from SEQ ID NOs: 4 to 9.

10. The method according to claim 5, wherein the human cell sample is whole blood and/or non-trypsinized tissue.

11. The method according to claim 1, wherein step b) further comprises detecting the amplicon with a probe comprising a nucleic acid sequence that hybridizes to a region of the amplicon.

* * * * *